United States Patent [19]
Davis, Jr.

[11] Patent Number: 5,269,800
[45] Date of Patent: Dec. 14, 1993

[54] BLOOD LANCING DEVICE

[75] Inventor: D. J. Davis, Jr., Carol Stream, Ill.

[73] Assignee: Davis Manufacturing Systems Inc., Wheaton, Ill.

[21] Appl. No.: 988,471

[22] Filed: Dec. 10, 1992

[51] Int. Cl.⁵ .............................................. A61B 17/32
[52] U.S. Cl. ................................. 606/182; 606/181; 606/167; 606/185
[58] Field of Search ................ 128/770; 604/115, 117, 604/158, 162, 172; 606/167, 172, 181, 182, 183, 184, 185, 188

[56] References Cited

U.S. PATENT DOCUMENTS

| | | |
|---|---|---|
| 3,659,608 | 5/1972 | Perry . |
| 3,760,809 | 9/1973 | Campbell, Jr. . |
| 3,901,243 | 8/1975 | Reed . |
| 4,191,190 | 3/1980 | Hastings .............................. 606/188 |
| 4,452,243 | 6/1984 | Leopoldi et al. . |
| 4,539,988 | 9/1985 | Shirley et al. . |
| 4,715,374 | 12/1987 | Maggio . |
| 4,980,109 | 12/1990 | Yamamoto et al. ................. 264/135 |
| 4,983,178 | 1/1991 | Schnell . |

*Primary Examiner*—C. Fred Rosenbaum
*Assistant Examiner*—Noelle Kent Gring
*Attorney, Agent, or Firm*—Welsh & Katz, Ltd.

[57] ABSTRACT

A device for lancing fingers and related body portions for purposes of drawing blood comprising opposing arms integrally joined at an acute angle. A lancing blade at one end is poised for travel through an aperture in the opposing arm, and separated until use by mating stop members. Pressure on the upper arm causes the stop members to slide past one another and the blade snaps through the aperture to lance the finger, whereupon it immediately retracts to an unexposed position.

11 Claims, 1 Drawing Sheet

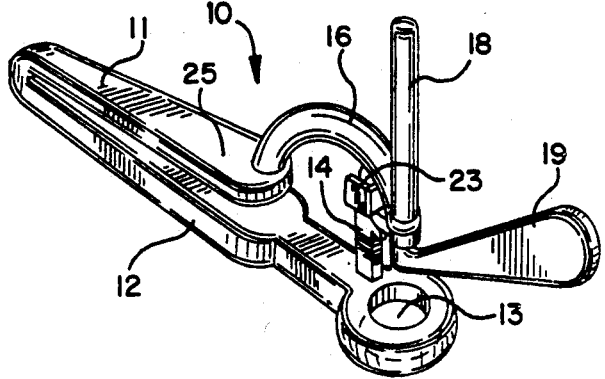
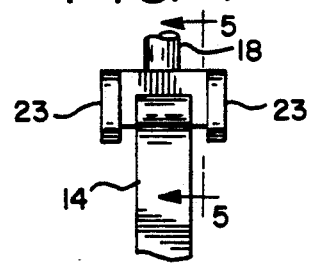
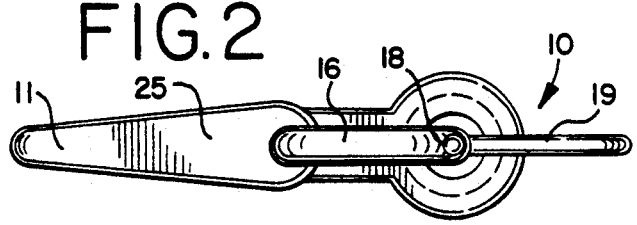
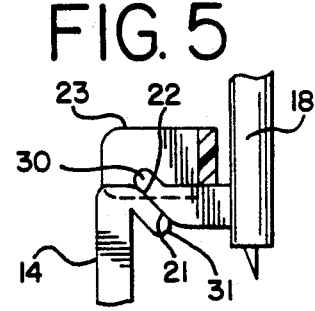
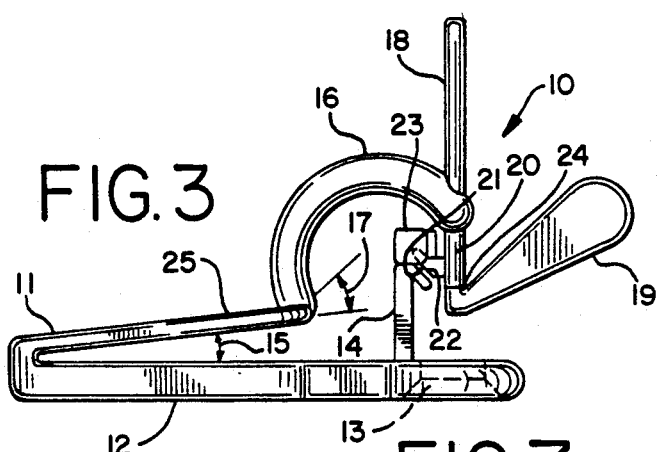
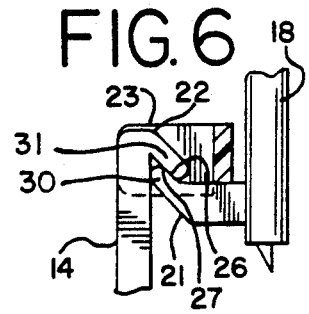
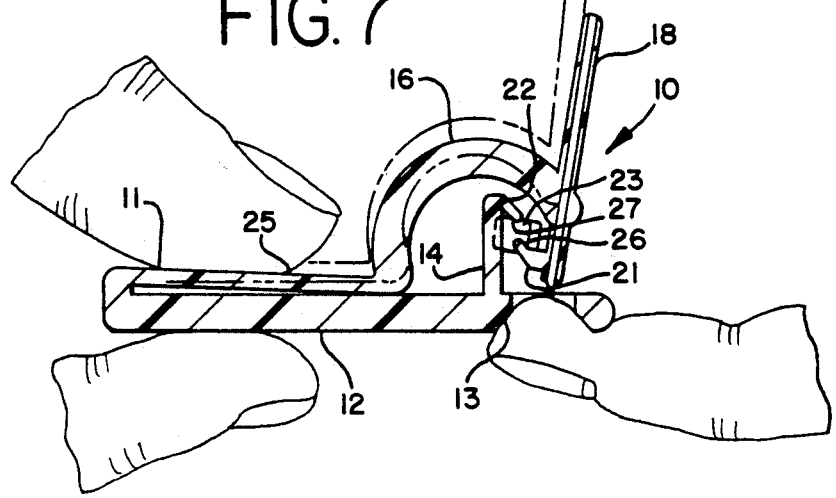

BLOOD LANCING DEVICE

BACKGROUND OF THE INVENTION

This invention relates to a surgical lancet for drawing blood for collection and analysis. More particularly, this invention relates to a disposable one-use lancet for the drawing of blood.

In certain blood collection procedures, only a small amount of blood is necessary, which small amount may be procured through a lancing technique with a simple pinlike lance mounted in a plastic handle and used with a stabbing motion. However, the use of this pin-like device requires a certain amount of skill to aim and stab to the required depth. Too shallow of a stab will result in insufficient blood, while too deep of a stab may cause excessive pain. In addition, the lancing device should be sterile and easy to use. Thus, a single use, disposable lancing device holds attraction as it would avoid the risk of cross-contamination and the possible spread of infectious disease from this source.

Accordingly, it is an object of the subject invention to provide an improved lancing device for lancing a finger or other skin area of the patient for the purpose of obtaining a blood sample.

Another object of the subject invention is to provide a lancing device at a low cost to make single use and disposability possible.

Another object of the subject invention is a blood lancing device which operates with a positive action lancing movement.

The above objects are accomplished with the device of the subject invention which comprises essentially a V-shaped spring member having a coacting pair of arms. A lancing blade is carried in a transverse position on an upper arm and positioned for reciprocal movement through and away from an opening in the opposing arm. In use, the opening is positioned over a position of the finger and the lancing blade used to draw blood as will be described. A cocking device located about the opening interacts with and limits movement of the lancing blade by means of a catch member both before and after use. The outer end portions of the upper arm may be flexed outwardly into a cocked position, whereby the catch member rests on a pressure release member and is held there by engagement of the release member with the catch member. By applying downward pressure on the lancing blade arm, the outer flexible portion of the lancing blade arm is caused to flex outwardly, whereby the catch member disengages from the release member and the lancing blade is propelled downward through the opening to lance the skin underneath. Guide sidewalls on the catch member assure proper vertical movement of the lancing blade. The resiliency of the trigger arm immediately pulls the lancing blade back where further cocking and use may be prevented by interaction of the release member with the catch member.

Further objects and advantages of the subject invention will become apparent to those skilled in the art from review of the following description, reference being made to the accompanying drawings in which,

BRIEF DESCRIPTION OF THE DRAWINGS

FIG. 1 is a perspective view of an embodiment of the subject invention showing the lancing blade and lancing opening.

FIG. 2 is a top view of the embodiment of FIG. 1.

FIG. 3 is a side view of the embodiment of FIG. 1.

FIG. 4 is a front view of the embodiment of FIG. 1, showing the positioning of the catch arm and cocking arm.

FIG. 5 is a side view of FIG. 4.

FIG. 6 is a side view showing the capture of the catch arm by the cocking arm after use.

FIG. 7 is a side view in partial cross section of the embodiment of FIG. 1 in use.

DETAILED DESCRIPTION OF THE INVENTION

Referring now to FIGS. 1 and 3, the lancing device 10 of the subject invention has a pair of arms 11 and 12 which are generally in a V-shaped relation with one another. Lower arm 12 comprises a straight base having a lancing aperture 13 at one end and a cocking arm or member 14 as will be described later in more detail. At the opposite end, base portion 12 is integrally connected to upper lancet arm 11 in a V-shaped connection. Upper lancet arm 11 extends outwardly from base portion 12 preferably at an angle 15 of from 5°–7°, and preferably 6°. At its outer end of upper lancet arm is a resilient arcuate or arm portion 16. While shown as an arcuate portion, resilient arm portion 16 may take any other shape which would provide increased resiliency at its outer end. Preferably arcuate portion 16 has an arc length of a half circle, which is disposed at an angle 17 of from about 25°–35°, preferably 30°, to the upper lancet arm 11. Arcuate portion is preferably a rod in cross-section with a diameter of approximately ⅛".

Secured to the extreme outermost tip of arm portion 16 is lancet blade 28 within lancet holder arm 18. Arm 18 is secured to resilient arm portion 16 in its midsection. Lancet blade 28 is preferably surgical steel or the like, and is carried by arm 18 for travel through opening 13. The entire assembly is a one-piece insert injection-molded plastic piece, made as well known in the art. The lancing device may be molded of a suitable thermoplastic such as nylon, polyvinylchloride, polyethylene, or polypropylene, preferably of polycarbonate.

Lancing blade 28 has a sharp end which is initially covered with a plastic sheath 19 which is scored at its connection 24 with the lower end of the resilient arm portion 16. The sheath 19 is preferably oriented so that it extends radially away from the lancing blade 28 and might be easily grasped and twisted off prior to use to expose the sharp end thereof. Extension of sheath 19 radially from the plane of the lancet blade 28 permits easy rotation of the sheath to break the score line and remove the sheath.

At the lower end of arm 18 is catch arm member 30 which interacts with cocking arm member 31 as will be described. Catch member 30 and cocking arm member 31 each have mating parallel 45° generally sloped surfaces 21 and 22, respectively, which are in contact with one another. More specifically, the upper catch arm surface 21 is generally flat and at a 45° angle to the horizontal, while lower cocking arm surface 22 is radiused, preferably with a 14" radius. Upper catch arm surface 21 may be rounded on an upper extremity. In this manner, sufficient friction is exhibited between the two surfaces 21 and 22 to maintain the respective arms in a cocked and ready position, yet great force is not required to overcome it which actuating the lancing procedure, as might be experienced with two flat opposing surfaces. Guide ears 23 are positioned on either side of the upper surface of catch member 20.

In the cocked position, the upper catch member 20 has a sloped contact surface 21 resting on mating sloped surface 22 of the lower cocking member 14. Ears 23 restrict lateral movement of the catch member 20.

In the use and operation of the subject invention, the lancet blade is exposed by twisting off sheath 19. During the twisting movement of the sheath to break the score line 24, lateral movement of the lancet blade is restricted, as stated, so that the mating surfaces do not lose contact with one another and attain a position inconsistent with a proper stabbing orientation and thrust.

Upper arm 11 has a finger or thumb pad 25 in its mid-section which permits the application of pressure in a downward direction. After exposing the lancet blade by removal of the sheath 19, and application of pressure on the thumb pad 25, flexible member 16 flexes until sufficient pressure is applied between mating surface portions 21 and 22, whereupon the catch member 30 slides off cocking arm surface 21 and the lancing blade snaps forcefully downward and towards and through aperture 13. When the lancing device 10 is placed on a finger, centering the aperture 13 on the portion of the finger to be lanced, as in FIG. 7, and this procedure carried out, the action of the lancing blade traveling forcefully through the aperture 13 causes the finger to be lanced. The resilient spring action of the upper arm 11 in conjunction with the resilient portion 16 causes the blade to snap back, out of the finger. Further movement of the lancing blade upward is restricted through contact of the upper surface 26 of the catch member with the lower surface 27 of the cocking arm. A second use of the lancing blade is made difficult by the ears which restrict lateral movement of the lancing blade so that it becomes very difficult to reposition the lancing blade in the cocked position. Therefore, the user is encouraged to disgrace of the device after one use.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

What is claimed is:

1. A lancing device, comprising:
   a base arm having inner and outer end portions;
   a resilient arm having an inner end integrally connected to said base arm inner portion at an angle of about 5°-7° and having an outer resilient arm portion comprising a half-circle connected to an inner spring arm at an angle of about 25° to about 35°;
   an aperture on said outer end portion of said base arm;
   a lancing blade carried on said outer spring arm portion for movement into and out of said aperture;
   mating first and second stop means on said base arm and said resilient arm respectively, for restricting movement of said resilient arm relative to said base arm;
   whereby upon application of downward force to said resilient arm, said first and second stop members disengage and cause said lancing blade to travel through said aperture to a lancing position, and thereafter retract to a nonlancing position.

2. The lancing device of claim 1 wherein said first and second stop members having opposing angled surfaces.

3. The lancing device of claim 2 wherein said second stop member has a pair of ears on an outer portion thereof for restricting lateral movement of said lancing blade.

4. The lancing device of claim 1 wherein said outer resilient arm portion is a rod in cross-section.

5. The lancing device of claim 1 further including a removable sheath about said lancing blade.

6. The lancing device of claim 1 wherein said device is formed by insert-injection molding.

7. The lancing device of claim 1 wherein said device is formed of polycarbonate.

8. The lancing device of claim 1 wherein said outer spring arm comprises a ⅛" rod.

9. The lancing device of claim 1 wherein said inner spring arm tapers in width, the end adjacent to said outer spring arm portion being wider than the opposing end.

10. A lancing device, comprising:
    a base arm having inner and outer end portions;
    a arm having an inner end and an outer end, said inner end integrally connected to said base arm inner end portion and having an outer arm portion comprising a semi-circle connected to said outer end portion;
    a pair of ears on said outer end portion;
    an aperture on said outer end portion of said base arm;
    a lancing blade carried on said outer spring arm portion for vertically movement into and out of said aperture, said ears restricting lateral movement of said blade while permitting said vertical movement;
    mating first and second stop means on said outer end portion and said outer arm respectively, for restricting said vertical movement of said spring arm relative to said base arm;
    whereby upon application of downward force to said spring arm, said first and second stop members disengage and cause said lancing blade to travel through said aperture to a lancing position, and thereafter retract to a nonlancing position.

11. The lancing device of claim 10 wherein said first and second stop members have opposing angled surfaces, one of which is radiused and the other of which is flat.

* * * * *